United States Patent [19]

Rudzena et al.

[11] Patent Number: 5,217,432
[45] Date of Patent: Jun. 8, 1993

[54] AUTOMATED DRUG INFUSION MANIFOLD

[75] Inventors: William L. Rudzena, McHenry; Wayne F. Adolf, Mount Prospect; Lois L. Caron, McHenry; Edward S. Tripp, Park City, all of Ill.

[73] Assignee: Abbott Laboratories, Abbott Park, Ill.

[21] Appl. No.: 815,682

[22] Filed: Dec. 31, 1991

[51] Int. Cl.⁵ .............................................. A61M 5/14
[52] U.S. Cl. ........................................ 604/80; 604/83; 604/173
[58] Field of Search ............................... 604/80-83, 604/89, 90, 169, 173, 905

[56] References Cited

U.S. PATENT DOCUMENTS 4,063,555 12/1977 Ulinder ................................. 604/83
4,795,441 1/1989 Bhatt ................................. 604/80 X
4,915,688 4/1990 Bischof ................................. 604/83

Primary Examiner—John D. Yasko
Attorney, Agent, or Firm—A. Nicholas Trausch, III

[57] ABSTRACT

A drug infusion manifold that includes a housing defining a plurality of spaced apart fluid chambers that have a closed first end portion and an opposing second end portion. The second end portions of immediately adjacent chambers are in fluid communication through channels extending therebetween. A plurality of spaced apart fluid inlets are formed in the housing in fluid communication with a corresponding fluid chamber. A check valve means is provided in each fluid chamber for directing drugs and/or solutions from the inlets into the chamber and precluding fluid flow from the chamber. An outlet is formed in the housing in direct fluid communication with at least one of the chambers.

13 Claims, 4 Drawing Sheets

AUTOMATED DRUG INFUSION MANIFOLD

RELATED APPLICATION

This application is related to U.S. patent application Ser. No. 07/632,254, filed on Dec. 21, 1990 now abandoned.

BACKGROUND OF THE INVENTION

1. Field Of The Invention

This invention relates to a device for controlling the infusion of drugs and/or other solutions. More specifically, the invention relates to an automatic drug infusion manifold that may be used to intravenously administer drugs, such as anesthetic and cardiovascular drugs, without the use of manually operated switches and with minimal common mixing volume.

2. Description Of The Prior Art

During surgery, and other medical procedures in an intensive care unit, a cardiovascular care unit, or an emergency room, it is necessary to administer different drugs to a patient in a selected and controlled manner. One procedure currently being used to administer such drugs is by individual syringes. Each syringe is connected to a stopcock which in turn is used with a primary (or patient) IV set. The medical provider must manually rotate the knob, handle, control lever, etc. of the stopcock in order to administer the selected drug to the patient. Depending on the location of the stopcock and the inside diameter of the IV tubing, there may be a large common volume in which different drug residuals may mix. Depending on the particular drugs, such mixing may have adverse effects on the patient, particularly in cardiovascular drug infusion.

Another system that has been used to administer selected drugs to a patient includes a common manifold device having multiple inlet drug lines that are controlled by individual stopcocks. Similar type devices have been proposed that include various types of valve arrangements in the inlet drug lines to control the infusion of drugs through the inlet drug lines while preventing backflow therethrough. Examples of these types of drug infusion devices are disclosed in U.S. Pat. Nos. 4,666,429, 4,819,684, 4,871,353, 4,908,018 and 4,915,688.

In U.S. Pat. No. 4,346,704 a parenteral solution administration device is disclosed that includes an outer housing defining an outlet tube and an inner tubular support defining an inlet tube. The support has a closed forward end positioned within the outer housing and has lateral apertures through which the bore of the tubular support communicates with the outlet tube. An elastic tube or sleeve surrounds the tubular support in covering relationship with the lateral apertures. The inner tubular support is free of retaining structure at its closed end so as to permit the elastic tube to slide laterally on the tubular support through a limited distance. Upon pressurized fluid flow through the inlet tube, the elastic tube is expanded by pressurized fluid passing through the apertures to permit fluid flow between the tube and tubular support out of both ends of the elastic tube.

In U.S. Pat. No. 4,063,555 a cannula assembly is disclosed that includes a housing defining a fluid flow passage having two fluid inlets and one fluid outlet. One of the fluid inlets is shaped to receive the tip of an injection syringe for introduction of fluid to the inlet. Fluid flow through the inlet is controlled by a check valve housing an elastic tubular valve member closing off outlet openings associated with the check valve. Under sufficient pressure of a fluid in the inlet, the tubular valve member deflects outwardly permitting flow through the outlet openings.

There is a need for a drug infusion manifold for controlling the infusion of selected drugs that does not need to be manipulated by hand and does not require manual switching operation. There is also a need for such a device that minimizes the volume of drug residual in the line and yet is still simple in design, reliable and inexpensive to manufacture. There is a need for a device in which the carrier fluid reliably flushes residual drug from the common areas so as not to compromise the action of later administered drugs. There is also a need for such a device that is compact and may be taped to the arm, back of the hand of a patient, or other administration areas.

SUMMARY OF THE INVENTION

A drug infusion manifold is provided that includes a housing defining a plurality of spaced apart fluid chambers that have a closed first end portion and an opposing second end portion. The second end portions of immediately adjacent chambers are in fluid communication through channels extending therebetween. A plurality of spaced apart fluid inlets are formed in the housing in fluid communication with a corresponding fluid chamber. A check valve means is provided in each fluid chamber for directing drugs and/or solutions from the inlets into the chamber and precluding fluid flow from the chamber. An outlet is formed in the housing in direct fluid communication with at least one of the chambers and in fluid communication with the other chambers through the channels.

In accordance with a unique feature of the invention, the check valve means includes a valve stem portion that extends into the fluid chamber. The valve stem portion has a side wall that defines an inlet passage that is open at one end in communication with a corresponding fluid inlet and is closed at the other end. The side wall is spaced from the inner surface of the inlet and has at least one lateral inlet port extending therethrough communicating the inlet passage with the fluid chamber. The valve stem has an elastomeric sleeve member that is received in covering relationship with the inlet port such that when the pressure of the drug and/or solution in the inlet passage exceeds a predetermined level the sleeve member deflects outwardly directing fluid flow from the inlet passage into the fluid chamber.

The housing comprises an integrally formed inlet section and an integrally formed outlet section that are assembled together. The outlet section defines the outlet and the fluid chambers. The second end portions of the fluid chambers open through a substantially flat surface of the outlet section and the channels are formed into this flat surface between adjacent fluid chambers. The inlet section defines the fluid inlets and the valve stem portions of the check valve. The open end portions of the valve stem portions extend outwardly from a substantially flat surface associated with the inlet section that is in facing relationship with the flat surface associated with the outlet section. The longitudinal movement of the sleeve member on the valve stem portion is limited between the flat surface associated with the inlet section and a substantially flat surface associated with the closed first end portion of the chamber so as to retain the sleeve member on the valve stem portion in covering relationship with the inlet port.

DESCRIPTION OF THE DRAWING

A better understanding of the drug infusion manifold of the invention will be had by reference to the drawings wherein.

DESCRIPTION OF THE PREFERRED EMBODIMENT

Figure 1:
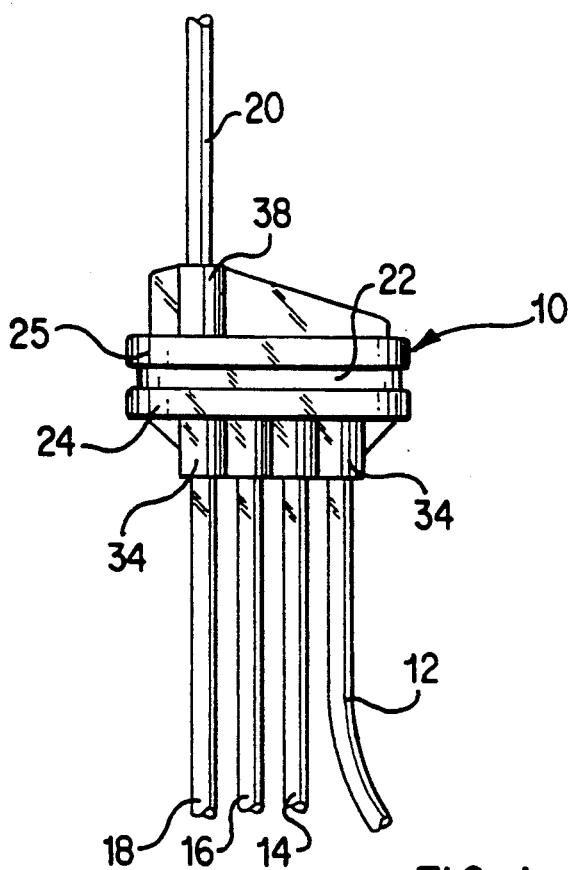
FIG. 1 is an elevational view of a drug infusion manifold constructed in accordance with the invention.
Figure 2:
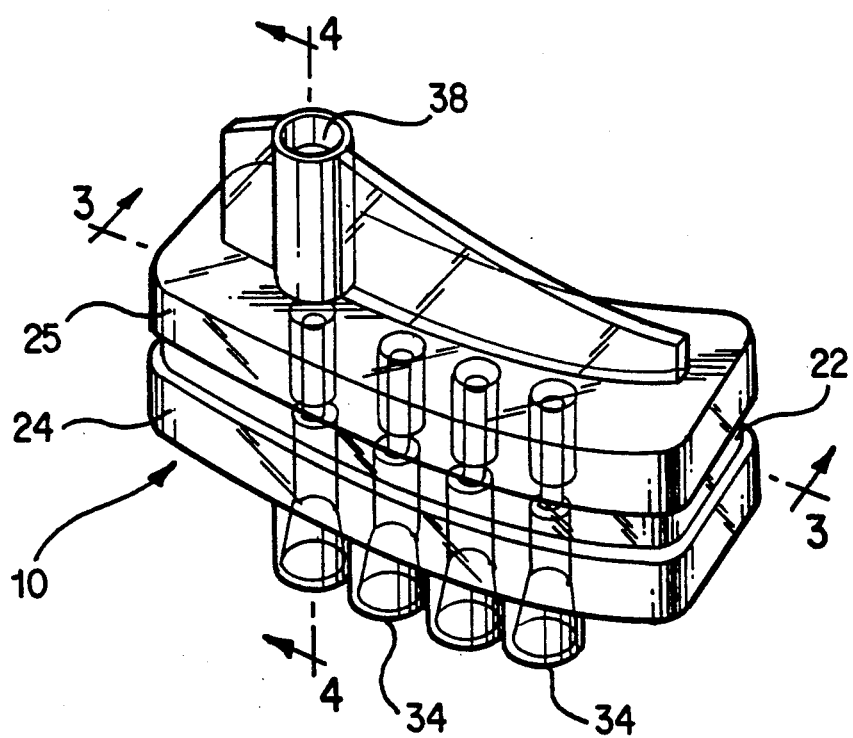
FIG. 2 is an enlarged perspective view of the drug infusion manifold of the invention.

FIG. 1 illustrates a drug and/or solution infusion manifold 10 constructed in accordance with the present invention that is intended to administer intravenous anesthetic or cardiovascular drugs and/or solutions into a patient during surgery, intensive care unit, cardiovascular care unit or emergency room procedures. The manifold 10 is shown attached to a carrier fluid inlet line 12, drug inlet lines 14, 16 and 18 and a short patient outlet line 20. Carrier fluid inlet line is attached to a source of carrier fluid, such as a flexible IV bag or glass bottle (not shown). The drug inlet lines 14, 16 and 18 may be attached to a suitable drug or solution pumping device, such as a peristaltic or syringe pump (not shown). The outlet line which should be as short as possible may be attached to a conventional patient catheter (not shown).

Referring to FIGS. 1–10, a preferred embodiment of a drug infusion manifold 10, incorporating features of the invention, includes a housing 22 comprising an inlet section 24 and an outlet section 25 that are assembled together in a manner that will be described hereinbelow. Housing 22 defines a plurality of spaced apart fluid chambers 26 formed in outlet section 25. Each chamber 26 has a closed first end portion 28 and an open second end portion 30. The second end portions 30 of immediately adjacent chamber 26 are in fluid communication through channels 32 formed in outlet section 26. A plurality of spaced apart fluid inlets 34 are formed in inlet section 24 that communicate with a corresponding chamber 26. A check valve 36 extends into each of the chambers 26 for directing drugs and/or solutions from the inlets 34 into the chambers 26 and precluding fluid flow from the chambers 26 back into the inlets 34. An outlet 38 is formed in outlet section 25 in fluid communication with one of the chambers 26 through a passage 39. Outlet 38 communicates with the other chambers 26 through the chambers 26 and channels 32.

Outlet 38 defines a socket that is preferably configured to form a high pressure joint for bonding a medical tubing 20 therein. The short tube 20 preferably ends with a low volume male luer fitting for receipt of a cooperating female luer fitting associated with the patient catheter. The illustrated preferred embodiment has four inlet sockets 34 that are configured to form high pressure joints for bonding to medical tubing fittings associated with the inlet lines 12, 14, 16 and 18. It will be understood that it is anticipated that alternative embodiments are envisioned that have either fewer or a greater number of inlet sockets 34.

Figure 3:
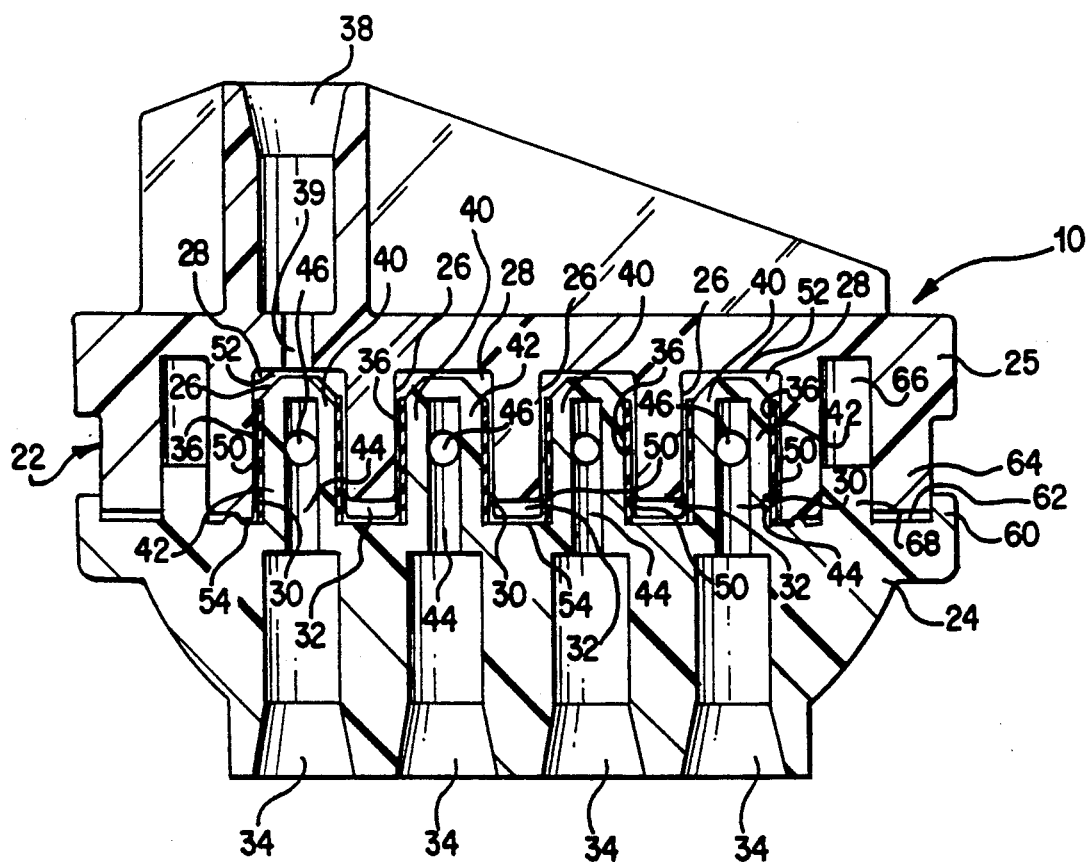
FIG. 3 is an enlarged sectional view taken along line 3—3 in FIG. 2.
Figure 4:
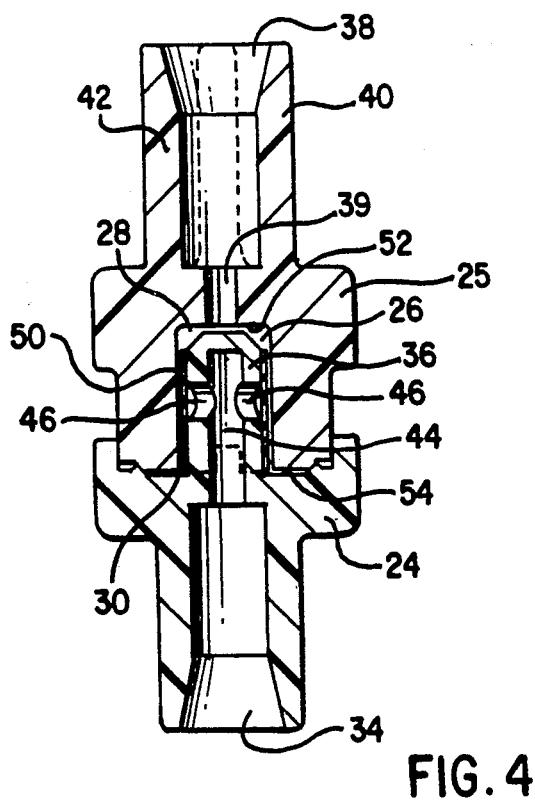
FIG. 4 is an enlarged sectional view taken along line 4—4 in FIG. 2.
Figure 6:
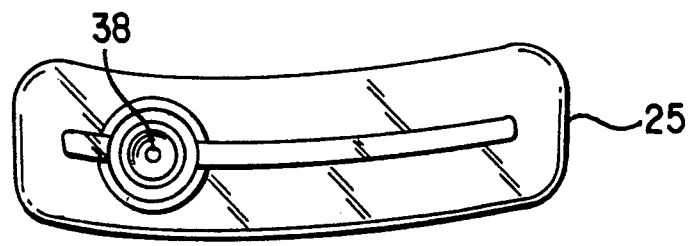
FIG. 6 is a top plan view of the outlet section of the housing shown in FIG. 5.
Figure 5:
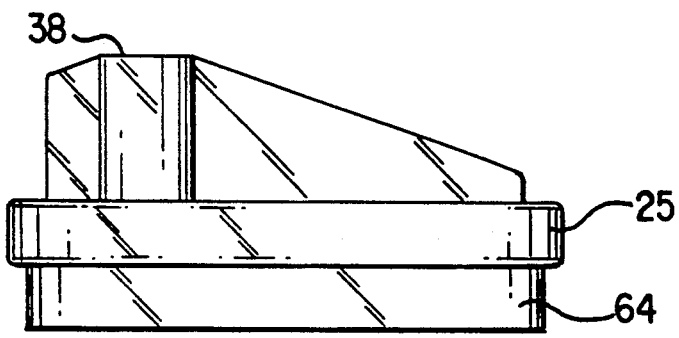
FIG. 5 is an elevational view of the outlet section of the housing of the drug infusion manifold shown in FIGS. 1-4.
Figure 7:
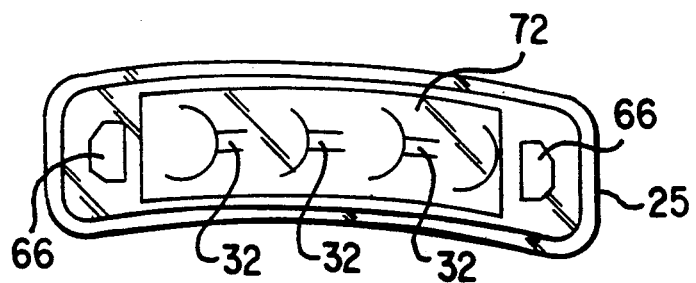
FIG. 7 is a bottom plan view of the outlet section of the housing shown in FIG. 5.
Figure 9:
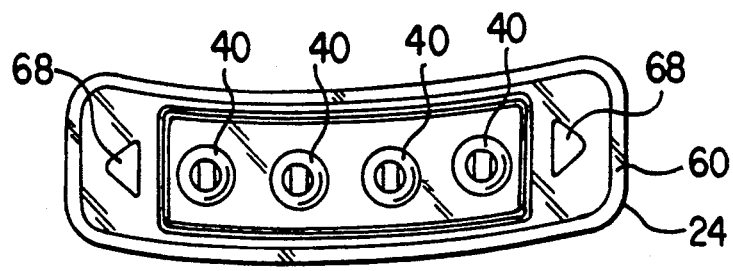
FIG. 9 is a top plan view of the inlet section of the housing shown in FIG. 8.
Figure 8:
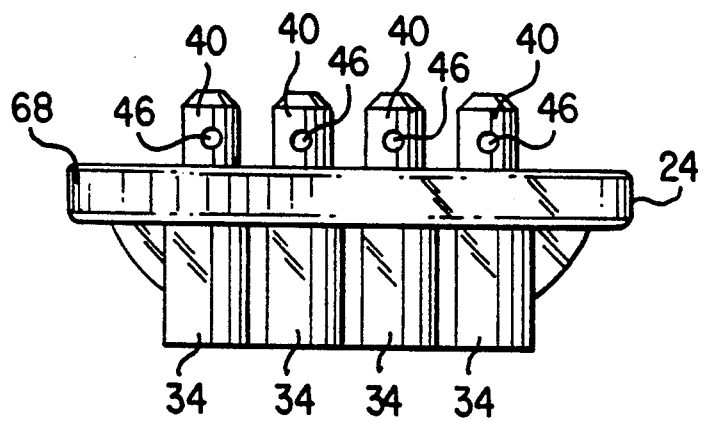
FIG. 8 is an elevational view of the inlet section of the housing of the drug infusion manifold shown in FIGS. 1-4.
Figure 10:
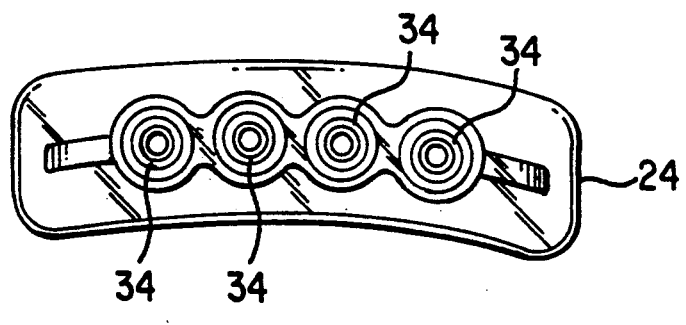
FIG. 10 is a bottom plan view of the inlet section of the housing shown in FIG. 8.

Each check valve 36 includes a valve stem portion 40 that is formed integrally with the inlet section 24 and extends into a corresponding chamber 26. Valve stem 40 has a side wall 42 that defines an inlet passage 44 that is open at one end in communication with a corresponding inlet 34 and is closed at its other end. The side wall is spaced from the inner surface of the chamber 26 and has lateral inlet ports 46 extending therethrough communicating the inlet passage 34 with the chamber 26. The closed end of the valve stem 40 is positioned a short distance from the closed end of chamber 26, as best seen in FIG. 3.

An elastomeric sleeve member 50 is positioned around valve stem 40 in covering relationship with ports 46. Sleeve member 50 is preferably an extended length of silicone tubing. The closed end of valve stem 40 is preferably chambered so as to facilitate the assembly of sleeve member 50 around valve stem 40. It is anticipated that sleeve member 50 may move longitudinally along the length of valve stem 40 during operation of manifold 10. The longitudinal movement of the sleeve member is limited as it contacts a substantially flat surface 52 defining the closed end of chamber 26 and a substantially flat surface 54 from which the valve stems 40 extend outwardly therefrom. The surfaces 52 and 54 are spaced apart so as to ensure that the sleeve member 50 always remains on valve stem 40 in covering relationships with ports 46.

In order to facilitate the assembly of inlet section 24 and outlet section 25, the inlet section is formed with a flange portion 60 that extends about the periphery of surface 54 so as to define a recess portion 62. The portion 64 of outlet section 25 into which chambers 26 are formed is shaped and dimensioned to be received in recess 62. The outlet section 25 is formed with recesses 66 that receive cooperating stud portions 68 that extend outward from surface 62. A center portion of surface 62 of inlet section 24 may be formed with a shallow recess 70 that receives a cooperating outwardly extending portion 72 of outlet section 25. The inlet section 24 and outlet section 25 are heat, chemical, solvent or preferably ultrasonically welded together in a well known manner. The sections 24 and 25 are preferably shaped to form a generally curved housing 12 that conforms to the arm or back of the hand of patient.

The brief discussion of the above-described preferred embodiment of the invention that follows sets forth the cooperation between the above disclosed structural elements.

In use, the drug infusion manifold 10 is typically assembled in such a manner that the carrier fluid inlet line 12 communicates with a supply of carrier fluid (not shown) which may be an IV set having a carrier solution-containing bag elevated on a support pole. The patient feed outlet line 20 is attached to outlet 38 via a conventional socket joint. One, two or all three of the inlet lines 14, 16 and 18 are attached to a corresponding inlet 34 via conventional socket type joints. The other ends of the inlet lines are in communication with a suitable drug or solution pumping device that controls the metering of drug or solution into the inlet lines in a well known manner.

The carrier fluid flows into manifold 10 through line 12 and into the inlet 34 corresponding with the end chamber 26. At such time as it is necessary to infuse a particular drug or drugs or other solutions into the patient, the particular drug or solution is directed through an inlet line 14, 16 or 18 into a corresponding inlet 34.

The carrier fluid or the drug from the inlet 34 flows into a corresponding passage 44. When the pressure of the fluid in passage 44 exceeds the cracking pressure of the valve 36, the sleeve member 50 deflects outwardly communicating passage 44 with a corresponding chamber 26 through ports 46. In accordance with a preferred embodiment of the invention, the opening pressure required to maintain flow through the valve 36 is preferably from about 1 psig to about 5 psig, most preferably about 3 psig. The flow of the drug solutions and the carrier solutions mix and then flow between adjacent chambers 26 through channels 32 into the chamber 26 that communicates with outlet 38 through passage 39. The mixture is directed to the patient through line 20. When the pressure of the drug solution is less than the opening pressure of a corresponding valve 36, the corresponding sleeve member 50 returns to its original position in covering relationship with port 46 and the flow of drug solution into the chamber 26 is terminated.

After termination of the flow of a particular drug through a corresponding chamber 26, the residual of that particular drug in the chamber is minimal. The in-line flow of the carrier fluid through the chambers 26 around the valve stems 42 serves to flush drug residuals therefrom and deliver a total dose of the drug to the patient.

As can be appreciated from the above description of the invention, manifold 10 controls the infusion of selected drugs and does not require a manual switching operation. The manifold 10 permits the continuous delivery of the carrier solution. The manifold is activated by the drug pumping device requiring no manual manipulation, thereby permitting operation without use of either of the operator's hands. The residual volume of drugs in the manifold is minimal and the delivery of a total drug dose is achieved. This allows infusion of cardiovascular drugs. With small bore tubing (0.043 inches) and the reduced volume construction of the manifold as previously described herein, the common mixing volume can be minimized to the order of 0.15 ml. The construction of the present invention allows bolus and continuous infusion modes to be intermixed without concern for backflow and drug mixing. The manifold is also suitable for attachment to the patient at various administration sites. Further there is minimal risk of retrograde contamination with the check valves of the present invention. These advantages are achieved in a manner that is simple in design, reliable in operation, and inexpensive to manufacture.

The foregoing invention can now be practiced by those skilled in the art. Such skilled persons will appreciate that the drug infusion manifold of the present invention is not necessarily restricted to the particular preferred embodiments presented herein. The scope of the invention is to be defined by the terms of the following claims in the spirit and meaning of the preceding description.

What is claimed is:

1. A drug infusion manifold for use in intravenous administration of drugs and/or solutions to a patient, said drug infusion manifold comprising:
    (a) a housing defining a plurality of spaced apart fluid chambers, each of said fluid chambers having a closed first end portion and a second end portion that is in fluid communication through a channel extending between second end portions of immediately adjacent fluid chambers;
    (b) a plurality of spaced apart fluid inlets formed in said housing in fluid communication with a corresponding fluid chamber;
    (c) check valve means extending into each of said fluid chambers for directing drugs and/or solutions from said inlets into said fluid chambers and precluding fluid flow from said fluid chambers, said check valve means including a valve stem portion that extends into said fluid chamber, said valve stem portion having a side wall that defines an inlet passage that is open at one end in communication with a corresponding inlet and is closed at the other end, said side wall being spaced from the inner surface of said fluid chamber and having at least one lateral inlet port extending therethrough communicating said inlet passage with said fluid chamber, said valve stem portion having an elastomeric sleeve member received in covering relationship with said inlet port such that when the pressure of the drug and/or solution in said inlet passage exceeds a predetermined level said sleeve member deflects outwardly directing fluid flow from said inlet passage into said fluid chamber; and
    (d) an outlet in fluid communication with at least one of said fluid chambers and in fluid communication with the other of said fluid chambers through said channels.

2. The invention as defined in claim 1 wherein said housing comprises an inlet section and an outlet section that are assembled together.

3. The invention as defined in claim 2, wherein said outlet section defines said outlet and said fluid chambers.

4. The invention as defined in claim 3 wherein said outlets define joints for receipt of cooperating tube fittings.

5. The invention as defined in claim 4 wherein each of said sockets communicate with one of said fluid chambers through a passage extending therebetween.

6. The invention as defined in claim 3 wherein said fluid chambers are integrally formed in said outlet section.

7. The invention as defined in claim 6 wherein said second end portion of said fluid chambers open through a substantially flat surface of said outlet section and said channels are formed into said flat surface between adjacent fluid chambers.

8. The invention as defined in claim 2 wherein said inlet section defines said fluid inlets and said valve stem portions of said check valve means.

9. The invention as defined in claim 8 wherein said fluid inlets define joints for receipt of cooperating tube fittings.

10. The invention as defined in claim 7 where said open end portions of said valve stem portions extend outwardly from a substantially flat surface associated with said inlet section that is in facing relationship with said substantially flat surface associated with said outlet section.

11. The invention as defined in claim 10 wherein the longitudinal movement of said sleeve member on said valve stem portion is limited between said flat surface associated with said inlet section and a substantially flat surface associated with said closed first end portion of said fluid chamber so as to retain said sleeve member on said valve stem portion in covering relationship with said inlet port.

12. The invention as defined in claim 11 wherein said inlet section is formed with a flange portion that extends about the periphery of said substantially flat surface so as to define a recess portion that receives said substantially flat surface of said outlet section.

13. The invention as defined in claim 12 wherein said outlet section is formed with recesses that extend through its substantially flat surface and said inlet section is formed with stud portions that extend outward from its substantially flat surface, said stud portions extend into said recesses upon assembly of said outlet section and inlet section.

* * * * *

UNITED STATES PATENT AND TRADEMARK OFFICE
CERTIFICATE OF CORRECTION

PATENT NO. : 5,217,432
DATED : June 8, 1993
INVENTOR(S) : W.L. Rudzena; W.F. Adolf; L.L. Caron; E.S. Tripp It is certified that error appears in the above-identified patent and that said Letters Patent is hereby corrected as shown below:

Column 6, claim 1, line 11, change "a" to --an opposing--.

Signed and Sealed this

Fifteenth Day of March, 1994

Attest:

BRUCE LEHMAN

Attesting Officer     Commissioner of Patents and Trademarks